US011060971B2

(12) United States Patent
Mannebach

(10) Patent No.: US 11,060,971 B2
(45) Date of Patent: Jul. 13, 2021

(54) METHOD AND DEVICE FOR MONITORING THE QUALITY OF GASEOUS MEDIA

(71) Applicant: HYDAC ELECTRONIC GMBH, Saarbruecken (DE)

(72) Inventor: Horst Mannebach, Saarbruecken (DE)

(73) Assignee: HYDAC ELECTRONIC GMBH, Saarbruecken (DE)

( * ) Notice: Subject to any disclaimer, the term of this patent is extended or adjusted under 35 U.S.C. 154(b) by 258 days.

(21) Appl. No.: 16/311,772

(22) PCT Filed: Jun. 12, 2017

(86) PCT No.: PCT/EP2017/000682
§ 371 (c)(1),
(2) Date: Dec. 20, 2018

(87) PCT Pub. No.: WO2017/220189
PCT Pub. Date: Dec. 28, 2017

(65) Prior Publication Data
US 2019/0212260 A1      Jul. 11, 2019

(30) Foreign Application Priority Data

Jun. 25, 2016  (DE) .................... 10 2016 007 825.1

(51) Int. Cl.
*G01N 21/3504*     (2014.01)
*G01N 21/03*       (2006.01)
(Continued)

(52) U.S. Cl.
CPC ..... *G01N 21/3504* (2013.01); *G01N 21/0317* (2013.01); *G01N 21/94* (2013.01);
(Continued)

(58) Field of Classification Search
CPC ........... G01N 21/3504; G01N 21/0317; G01N 21/94; G01N 21/031; G01N 21/3536; G01N 21/354; G01N 2021/8578
See application file for complete search history.

(56) References Cited

U.S. PATENT DOCUMENTS 5,223,716 A     6/1993  Rossiter
6,941,230 B1    9/2005  Stirnberg et al.
(Continued)

FOREIGN PATENT DOCUMENTS

DE     199 00 129     8/2000
GB     2 466 181      6/2010
(Continued)

OTHER PUBLICATIONS

International Search Report (ISR) dated Sep. 14, 2017 in International (PCT) Application No. PCT/EP2017/000682.

*Primary Examiner* — Michael C Bryant
(74) *Attorney, Agent, or Firm* — Wenderoth, Lind & Ponack, L.L.P.

(57) ABSTRACT

A method and a device monitors the quality of gaseous media dispensed by a filling station, in particular hydrogen, by an infrared measuring system. The infrared measuring system is connected into the dispensing path of the respective gaseous medium extending from the filling station to a consumer, and measures the transmission of infrared radiation at different wavelengths and different pressures. From the transmission measurements, the concentration of contaminants, which influence the quality, is calculated. At least when predetrminable quality parameters are exceeded, this exceeding is indicated.

15 Claims, 4 Drawing Sheets

(51) Int. Cl.
*G01N 33/22* (2006.01)
*G01N 21/94* (2006.01)
*G01N 21/85* (2006.01)

(52) U.S. Cl.
CPC ......... *G01N 33/225* (2013.01); *G01N 21/031* (2013.01); *G01N 2021/354* (2013.01); *G01N 2021/3536* (2013.01); *G01N 2021/8557* (2013.01); *G01N 2021/8578* (2013.01)

(56) References Cited

U.S. PATENT DOCUMENTS

| | | | |
|---|---|---|---|
| 7,446,317 B2 | 11/2008 | Doyle | |
| 8,686,364 B1 * | 4/2014 | Little, III | G01J 3/28 |
| | | | 250/339.12 |
| 2011/0005302 A1 | 1/2011 | Ahmed et al. | |
| 2014/0360372 A1 | 12/2014 | Ahmed et al. | |
| 2015/0131093 A1 * | 5/2015 | Saptari | G01N 21/3518 |
| | | | 356/326 |
| 2017/0030829 A1 | 2/2017 | Saptari | |
| 2017/0314383 A1 * | 11/2017 | Ispirescu | G01N 21/65 |

FOREIGN PATENT DOCUMENTS

| | | |
|---|---|---|
| WO | 2013/139462 | 9/2013 |
| WO | 2016/173610 | 11/2016 |
| WO | 2016/195580 | 12/2016 |

* cited by examiner

METHOD AND DEVICE FOR MONITORING THE QUALITY OF GASEOUS MEDIA

FIELD OF THE INVENTION

The invention relates to a method and a device for monitoring the quality of gaseous media, in particular hydrogen, which can be dispensed at a filling station.

BACKGROUND OF THE INVENTION

WO 2013/139462 A1 discloses a test device for determining the particle load of pressurized hydrogen. The test device a housing contains a sampling chamber, in which a filter receptacle for a test filter is provided, through which a sample amount of hydrogen can flow during a test procedure and which, after the test procedure has been completed, can be removed from the sampling chamber for evaluating the depositions of particles. An adjustable throttle element is provided that allows a different degree of throttling of the flow entering the sampling chamber.

When initiating a test procedure with the known device, in which the initially unpressurized sampling chamber is connected to the source of pressurized hydrogen, for example, at a hydrogen fueling pump, the restrictor element can be used to set an initial restriction of the flow to prevent the test filter from being exposed to a harmful pressure surge. While this restrictor element avoids the risk of damage to the test filter due to an initial pressure surge, the throttling effect can be reduced for the further actual test procedure such that during refueling the flow through the test filter is at an optimum flow rate for the test result, which may for example be in the range of 60 g/sec, i.e. in a range that is suitable for refueling a vehicle.

As stated, such devices are primarily for use in hydrogen refueling systems or filling stations, i.e., especially in engine applications where hydrogen is used as gaseous fuel or for supplying fuel cells with hydrogen. For the failure-free operation of hydrogen-powered internal combustion engines as well as of fuel cells, the hydrogen has to be completely free of particulate foreign matter, which can be detected using such testing devices.

Although the known solution is very well suited for the detection of particulate contaminants in the hydrogen stream, gaseous impurities of hydrogen, which can also have a damaging effect on a hydrogen drive, in particular in the form of a fuel cell cannot be determined in this way.

SUMMARY OF THE INVENTION

Based on this prior art, the invention therefore addresses the problem of providing an improved method and a device for monitoring the quality of gaseous media, in particular hydrogen, dispensed at a filling station, which can also detect gaseous impurities. A method and a device according to the invention solve this problem.

In the method according to the invention, an infrared (IR) measuring device is used, which is connected in the dispensing path of the gaseous medium, in particular of hydrogen, from the filling station to a consumer. The IR measuring device measures the transmission of infrared radiation or infrared light at different wavelengths and pressures, computes the concentration of contaminants affecting the quality and displays that concentration at least if pre-definable quality parameters are exceeded.

Gaseous impurities in hydrogen, as they regularly result from the previous treatment (reforming) or from compressor damage, cause damage to the sensitive fuel cells of a motor drive amongst other things. Therefore, standards such as SAE J2719 or ISO/DIS 14647-2 specify purity requirements for hydrogen at hydrogen filling stations. Regularly occurring impurities of hydrogen besides water are hydrocarbons. Carbon monoxide and carbon dioxide occur as gaseous pollutants. Formaldehyde, formic acid and ammonia, each also in their gaseous forms, are present in the hydrogen gas as impurities. Further impurities can be formed by the gases oxygen, helium, nitrogen, argon and halogens and sulfur gas. All the above-mentioned gaseous impurities of hydrogen including water can be detected in the laboratory. Due to the variety of compounds and the low limit values, such a laboratory analysis is a major challenge and requires the use of several measurement methods, e.g., different methods of gas chromatography and ion chromatography. A direct transfer of these laboratory measurement methods to a sensor device for the online measurement of the hydrogen quality at a filling station is not possible.

The method of analysis having the greatest coverage of the particularly critical gaseous impurities in terms of the solution according to the invention is infrared spectroscopy. Infrared spectroscopy makes use of the fact that the substances to be detected absorb light in the range of the infrared spectrum. The absorption in every case occurs at substance-specific wavelengths. Not all substances are infrared active, not all absorb infrared light. Rather, infra-active substances must generally have a dipole moment. Symmetric molecules, such as the abovementioned oxygen, helium, nitrogen, argon and halogens, cannot be detected by the measuring method according to the invention because they lack a dipole moment. All other gaseous impurities in hydrogen mentioned above, however, can be detected based on infrared spectroscopy using the infrared measuring device according to the invention on site and online at a hydrogen filling station during refueling.

Particularly advantageous is the ability to perform the method according to the invention using the infrared measuring device online in spite of the high pressures during the dispensing of hydrogen at the filling station, without the refueling process being impaired by the quality assessment. In this way, a measuring log can be created online at the filling station, which is provided to the filling station user as proof of the purity of the released hydrogen to warrant the continued functioning of the fuel cell of his vehicle using the hydrogen of this refueling. A device according to the invention is used to perform the pertinent infrared measuring method using a high-pressure resistant infrared cuvette, having a pressure-resistant pipe section, in which a preferably galvanically gold-plated inner pipe is inserted as an infrared tube conductor and attached there. Preferably, closable ports as sampling inlet and a sampling outlet are used to supply hydrogen into or remove it from the pressure-resistant pipe section for an infrared measurement process by a suitable emitter and a suitable detector. The determined values can then be input into a control and processing unit, for example, for the creation of a measurement protocol or for the output of an alarm, which unit can also perform signal processing including pressure and/or temperature values of the hydrogen in online operation.

Further advantageous embodiments of the solution according to the invention are subject to the other dependent claims.

The method according to the invention will be explained in more detail with reference to a device according to the invention for performing this method.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings that form a part of this disclosure and that are schematic and not to scale.

DETAILED DESCRIPTION OF THE INVENTION

Figure 1:
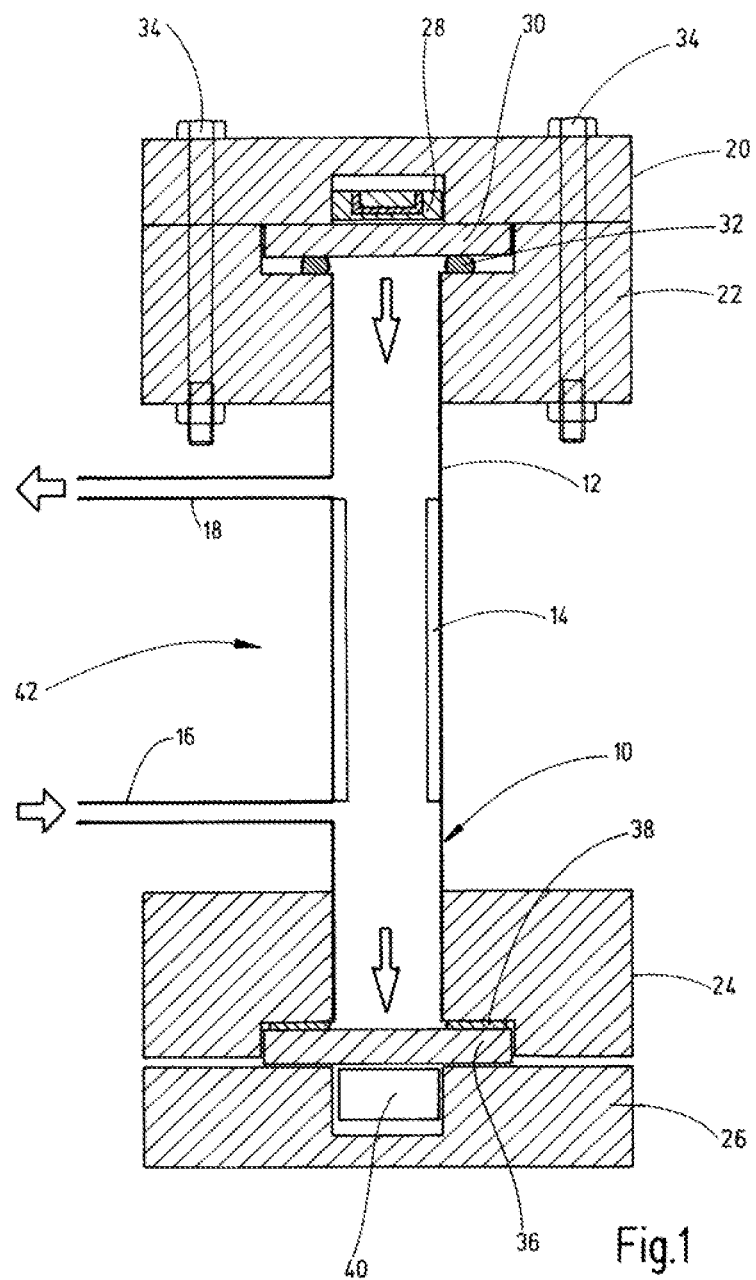
FIGS. 1 and 2 are side views in section of measuring devices according to first and second embodiments, respectively, of the invention.

The device according to the invention shown in FIG. 1 shows a highly pressure-resistant, infrared cuvette 10 having a pressure-resistant pipe section 12. An infrared waveguide 14, which is preferably formed as a galvanically gold-plated inner tube, is located inside the pipe section 12. In the pipe sections 12, the waveguide 14 is inserted and attached there according to the illustration of FIG. 1. Below the waveguide 14, a media-conducting tubular connection or port 16 opens into the pipe section 12. Another tubular connection or port 18 is above the waveguide 14. The port 16, as the arrow shows, is used for the supply of a gaseous medium. The port 18 is used for the discharge of the gas volume introduced into the pipe section 12. In principle, any gaseous media can be introduced and removed for investigation purposes. Below, however, only hydrogen gas is considered, which is supplied from a hydrogen filling station (not shown) at very high pressure, for instance in the range of 700 bar, as a sample to the infrared cuvette 10.

Flange parts assigned in pairs 20, 22 and 24, 26 adjoin at the opposite free ends of the pipe section 12. The first flange 20 arranged at the top in FIG. 1 has a central recess for receiving a high-power infrared emitter 28. Underneath and received in a recess of the second flange 22 is an infrared transmissive, high-pressure resistant window 30. At the front of window 30, an annular seal 32 is arranged for sealing the interior of the pipe section 12 from the environment. As further indicated in FIG. 1, the two flange parts 20 and 22 are connected to each other via a screw connection 34, including the annular seal 32 in a pressure-tight manner. Materials used for the window 30 are in particular silicon and germanium, which permit the passage of infrared radiation in a predeterminable wave range.

The flange part 24 terminating the tubular piece 12 at the bottom in turn has a central recess, into which a further infrared transmissive window 36 is inserted frontally on the upper side, which window ensures the sealing of the interior of the pipe section 12 towards the environment based on a soldered connection 38. An infrared detector 40 is then inserted in a central recess of the flange portion or part 26 beneath flange portion or part 24 for the evaluation of the received infrared spectrum. Consequently, the infrared emitter 28 or the infrared detector 40 is located in the unpressurized area behind the respective windows 30, 36.

In the high-pressure resistant cuvette 10, the volume concentration of the gaseous impurities increases in proportion to the pressure, such that e.g. for an inlet pressure of the hydrogen of 500 bar, the infrared absorption in the measuring cell is 500 times that of an inlet pressure of 1 bar. This measuring effect of the illustrated robust and cost-effective IR infrared measuring technology is based on this multiplication.

The measuring arrangement or measuring device shown in FIG. 1 then forms the infrared measuring device 42 provided for the method as a whole.

Figure 3:
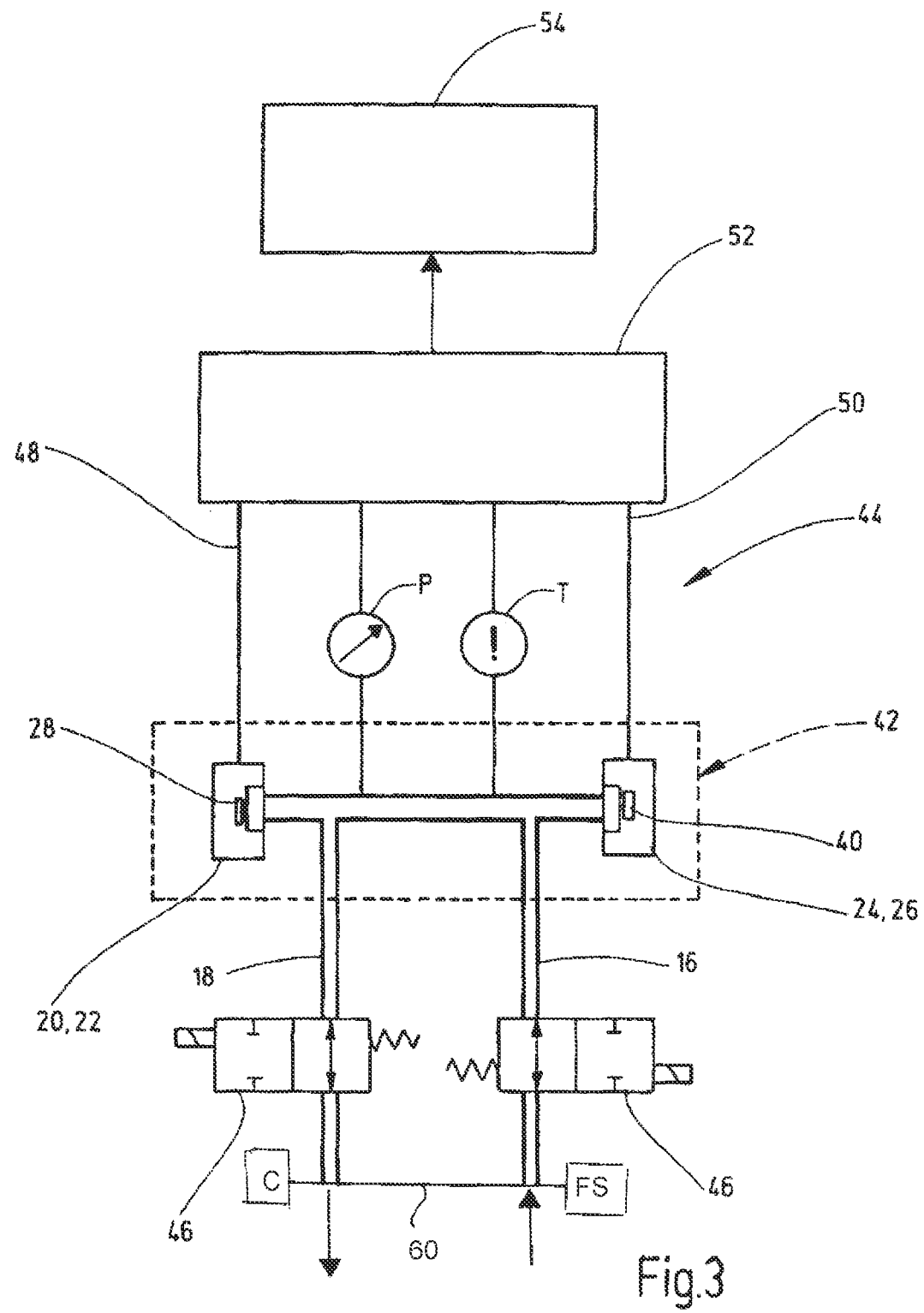
FIG. 3 is a schematic diagram of a supplemented device solution for the embodiment according to FIG. 1.

FIG. 3 shows, by way of example, the infrared measuring device 42 according to FIG. 1 is part of a total measuring device or system 44, which can be connected for the online measurement of gas impurities at a dispensing filling station FS, for example for hydrogen, with little installation effort. Solenoid 2/2-way valves 46 are connected in the ports 16, 18 to shut off the inflow and outflow of hydrogen gas. Consequently, the measuring device 44 can be used to take hydrogen gas samples via a bypass path formed by ports 16, 18 from the discharge line 60 connected in fluid communication with filling station FS and consumer C, and introduce it for a measurement process in the infrared cuvette 10 for an evaluation process after closing the directional control valves 46.

In this case, both the infrared emitter 28 and the infrared detector 40 are connected to signal processing electronics via respective electrical connecting lines 48 and 50, which electronics are shown in FIG. 3 in the form of a black box as a control and processing unit 52. In the relevant signal processing unit, the respective pressure value or the temperature value in the measuring section, formed by the interior of the pipe section 12, can be detected via corresponding pressure and temperature sensors P, T and used for the evaluation of the results determined optically. An output device 54 may be connected to the output side of the signal-processing control and processing unit 52, in turn, for example, which generates a measurement log on the quality (degree of contamination and nature of impurities) of the hydrogen dispensed by the filling station and preferably triggers an alarm if pre-definable quality parameters of the gas are exceeded.

Figure 2:
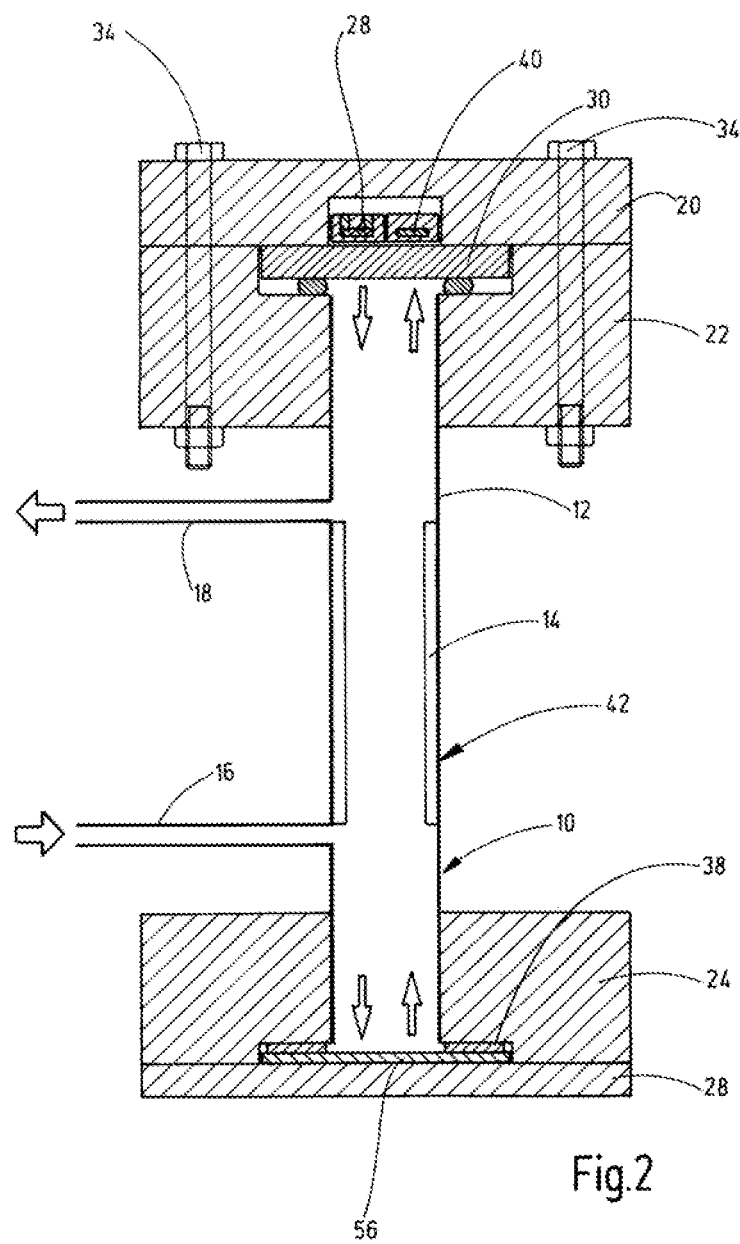

The embodiment of FIG. 2 largely corresponds to the infrared measuring device 42 according to the embodiment of FIG. 1 with the proviso that both the infrared emitter 28 and the infrared detector 40 are housed side by side in the upper flange portion 20 in the center recess. A further difference is a mirror 56 reflecting infrared rays. The mirror 56 is received at the lower end of the pipe section 12 in the third flange section 24 via a soldered connection 38. A screwed connection, not shown in greater detail, comparable to the screwed connection 34, is used to firmly connect the lower two flanges 24 and 26 to each other, such that the lower solder joint 38 achieves a pressure-tight termination of the interior of the pipe section 12 towards the environment. As the double-arrow representation in the interior of the pipe section 12 shows, the mirror 56 doubles the length of the travel measuring section between the emitter 28 and the detector 40 compared to the solution according to FIG. 1, which in this respect increases the measuring accuracy of the measuring device 42 according to the embodiment of FIG. 2 accordingly.

The proposed solution according to the invention is used to perform a method for monitoring the hydrogen quality at a hydrogen filling station (not shown in detail), having an overall measuring device 44 according to the exemplary embodiment of FIG. 3. That measuring device essentially has the high-pressure-resistant infrared cuvette 10 introduced above, an infrared emitter 28, an infrared detector 40 and at least one pressure sensor P and a control and processing unit 52. The measuring device 44 is integrated as a whole in the hydrogen filling station and is for measuring processes on demand periodically filled with hydrogen and vented by the valves 46. The infrared measuring device 42, 44 is then used to measure the transmission of infrared radiation or infrared light at different wavelengths and pressures, and the concentration of, in particular, gaseous impurities in the hydrogen, is computed therefrom. If the determined measured values give cause for concern, the output device 54 connected to the control and computing unit 52 in the form of an electronic signal processing can trigger an alarm if predefined limit values are exceeded.

Preferably, the control and computing unit 52 performs transmission measurements at different densities, buffers them and then subtracts them from each other. As already stated, a pressure sensor P can perform the pressure measurement to determine the density. The pressure measurement can be supplemented by a temperature measurement by a temperature sensor T.

The use of an infrared emitter 28, preferably a hotplate emitter, which emits a broadband infrared beam, has been found to be particularly advantageous for performing the method according to the invention. Furthermore, it is advantageous if the infrared detector 40 is a multi-channel detector having filters in the range between 1000 and 4000 wavenumbers. Advantageously, the infrared detector 40 is a spectrometer. If, as shown in FIG. 2, the emitter 28 and the detector 40 are located on the same side of the pipe section 12, i.e. in the upper flange part 20, only common electronics for the pertinent components 28 and 40 are required.

As will be explained in more detail below, the distribution of the detected infrared-active bands of the individual contaminants, plotted against the wave number, indicates the type of the individual impurity. For instance, ammonia gas is found as an impurity for wave numbers around 1000. The contaminants formic acid, water, carbon monoxide and carbon dioxide occur in the range of 2000 wave numbers. Wave numbers around 3000 indicate formaldehyde and hydrocarbons. Wave numbers just below 4000 again indicate water. As stated above, the relevant measurement range is between 1000 and 4000 wavenumbers, i.e. at wavelengths between 2.5 µm and 10 µm of the infrared radiation. The position of the absorption bands can therefore be used to identify a substance as such, and the attenuation of the infrared radiation as it passes through the hydrogen sample yields the concentration from Lambert-Beer's law as follows:

$$A = lg(I_0/I_1) = lg(I/T) = \varepsilon(\lambda) \cdot c \cdot d$$

where:
A: absorbance
$I_0$: intensity of irradiated light [W/m$^2$]
$I_1$: intensity of the attenuated light [W/m$^2$]
T=$I_1/I_0$: transmittance
$\varepsilon(\lambda)$: molar (decadal) absorption coefficient [m$^2$/mol]
c: concentration [mol/l]
d: travel length of the light beam through the sample [m]

The dependence of the absorption on the wavelength is reflected in the dependence of the molar absorption coefficient on the wavelength in Lambert-Beer's law.

Lambert-Beer's law outlines the standard approach for measuring small concentrations. At low concentrations, the length of travel d of the infrared light beam through the sample is increased. This can be effected by extending the measuring cell in the form of the cuvette 10 or by repeatedly irradiating the cuvette 10 using a mirror device with the mirror 56 as shown in FIG. 2. For the application mentioned here, however, the extension of the travel length d is a practical limit, and it has proved to be advantageous to form the pipe section 12 formed as a measuring section of FIGS. 1 and 2, preferably at a length of 500 mm. Lengths of 100 mm to 1500 mm are equally possible, too. Further, the diameter of the pipe section is 10, preferably 3 to 15 mm, more preferably 5 mm.

Furthermore, it is necessary to consider the concentration c, which constitutes yet another controllable quantity on the right-hand side of the above Lambert-Beer equation. C, as stated, denotes the concentration of the substance to be detected in the infrared cuvette 10 in mol/l. This parameter c can easily be increased significantly by an increase in pressure, which is particularly advantageous in the case of the hydrogen filling station, as the gas to be analyzed is already at very high pressure, for example of the order of 700 to 800 bar. The infrared spectra according to FIGS. 4 to 6 indicate that at the very high pressures of 700 bar, a significant measurement pattern (solid lines) immediately results, which is not the case at 1 bar (measurement lines shown in dashed lines).

Figure 4:
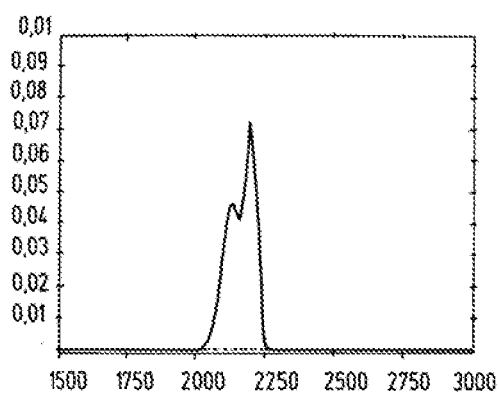
FIGS. 4 to 6 are graphs of different infrared spectra for carbon monoxide, carbon dioxide and ethane, respectively, wherein the ordinate showing absorbance A is plotted above the abscissa showing the wavenumbers in 1/cm.

The absorbance of the IR spectrum measured in FIG. 4 of about 0.06 for CO gas, at a concentration of 100 ppm, a pressure of 1 bar absolute and a path length of 10 m means that approx. 87% of intensity are transmitted at 2200 wavenumbers. However, the carbon monoxide limit set by standard SAE J2719 is only 0.2 ppm, i.e. one five-hundredth of the concentration of the measurement shown in FIG. 4. At this concentration the absorbance is 0.00012 and the transmission is 99.97%. This small change in transmission would be extremely difficult to detect using laboratory equipment. If the pressure is then increased to 700 bar in accordance with the solid line drawn in FIG. 4, the absorbance increases by a factor of 700. For a reduction of the travel length d from about 10 m to 500 cm according to the length of the pipe section 12 for the infrared cuvette 10, a factor of 20 for the absorbance is lost again, resulting in a value of 0.0042. However, this value again corresponds to a transmission of 99.03%. This reduction of almost 1% is easily detectable even using standard optical components. Similar estimates for water, hydrocarbons, carbon dioxide (see FIG. 5), formaldehyde, formic acid, ammonia and ethane (see FIG. 6) confirm the above observation and show that the deciding factor is the increase in concentration within the high pressure IR Cuvette 10, caused by the dispensing pressure of the hydrogen at the filling station.

Figure 5:
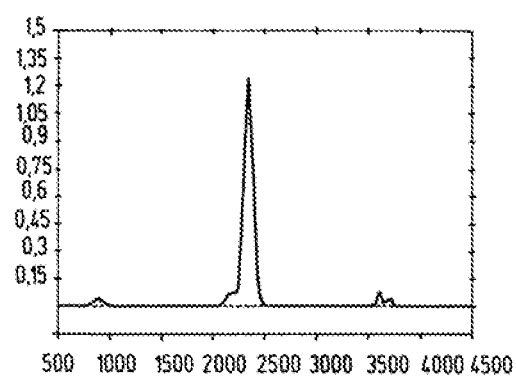
Figure 6:
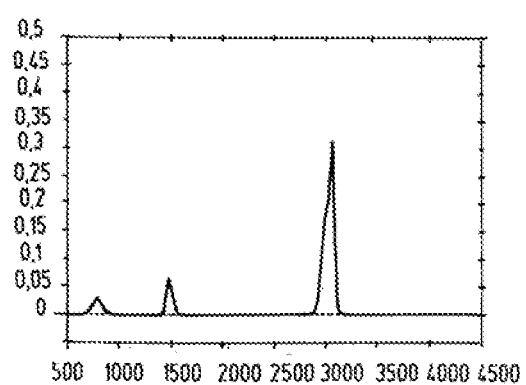

As FIGS. 4 to 6 finally show, gaseous impurities such as carbon monoxide (FIG. 4), carbon dioxide (FIG. 5) or ethane (FIG. 6) can be reliably detected in the hydrogen gas at high pressures using the device according to the invention described above according to FIGS. 1 to 3. If pre-definable limit values are exceeded, the hydrogen tank operation can advantageously be interrupted.

While various embodiments have been chosen to illustrate the invention, it will be understood by those skilled in the art that various changes and modifications can be made therein without departing from the scope of the invention as defined in the appended claims.

The invention claimed is:

1. A method for monitoring quality of gaseous media dispensable from a gas filling station, the method comprising the steps of:
   dispensing hydrogen gas from a hydrogen filling station to a consumer via a dispensing path;

conveying sequential samples of the hydrogen gas from the dispensing path to an infrared measuring device connected in fluid communication with the dispensing path, the infrared measuring device having a pipe section with an infrared wave guide in the pipe section;

checking the sequential samples in the infrared measuring device for impurities without interrupting concurrent dispensing of the hydrogen gas from the hydrogen filling station to the consumer via the dispensing path;

performing the checking of the sequential samples for the impurities by measuring transmissions of infrared radiation at different wavelengths and pressures in infrared measuring device; and computing concentrations of quality-influencing impurities from the transmissions to determine if predeterminable quality parameters of the hydrogen gas are exceeded.

2. A method according to claim 1 wherein
the impurities, which are infrared active, are detected by the infrared measuring device due to a dipole movement.

3. A method according to claim 1 wherein
the infrared measuring device uses infrared spectroscopy to determine types of the impurities from positions of absorption bands of the sequential samples and to determine the concentral concentrations of the respective quality-influencing impurities from attenuations of the infrared radiation passing through the sequential samples.

4. A method according to claim 1 wherein
the computing applies Lambert-Beer law for determining the concentrations of the quality-influencing impurities in the sequential samples.

5. A method according to claim 1 wherein
the performing of the checking of the sequential samples in the infrared measuring device is at pressures of at least 500 bar.

6. A method according to claim 5 wherein
the pressures are at least 700 bar.

7. A method according to claim 1 wherein
a control and processing unit of the infrared measuring device buffers transmission measurements of the sequential samples at different densities of the sequential samples and subtracts the transmission measurements from each other for determining the concentrations; and
pressure measurements of the sequential samples determine the densities.

8. A method according to claim 7 wherein
temperature measurements of the sequential samples are used in determining the densities.

9. A method according to claim 1 wherein
the sequential samples are conveyed from the dispensing path via a bypass path to the infrared measuring device connected in fluid communication by the bypass path to the dispensing path, the pipe section being in the bypass path, the pipe section extending along a longitudinal axis, having components of the infrared device located on opposite first and second axial ends of the pipe section and having first and second ports connected in fluid communication with the dispensing path, the first and second ports opening into the pipe section at spaced locations along the longitudinal axis between the first and second axial ends of the pipe section and extending radially through the pipe section relative to the longitudinal axis.

10. A method according to claim 1 wherein
the infrared wave guide comprises a galvanically gold-plated inner tube.

11. A measuring apparatus for monitoring quality of gaseous media dispensed from a hydrogen filling station, the measuring device comprising:

an infrared device capable of measuring transmissions of infrared radiation in sequential samples of hydrogen at different wavelengths and pressures, of computing concentrations of quality-influencing impurities in the sequential samples and of indicating whether the concentrations exceed predetermined quality parameters, the infrared device having a pressure resistant pipe section with an infrared wave guide in the pipe section; and a hydrogen filling station having a dispensing path connecting the hydrogen filling station in fluid communication with a consumer, the infrared measuring device being connected to the dispensing path allowing the sequential samples to be conveyed into the infrared measuring device and be analyzed for the quality-influencing impurities while hydrogen is dispensed from the hydrogen dispensing station to the consumer.

12. A measuring apparatus according to claim 11 wherein
the infrared measuring device comprises an infrared emitter, an infrared detector, a pressure sensor and a control and a processing unit.

13. A measuring apparatus according to claim 12 wherein
the pipe section comprises inlet and outlet ports connected in fluid communication to the dispensing path and an interior of the pressure resistant pipe section, the infrared waveguide being a galvanically gold-plate inner tube.

14. A measuring apparatus according to claim 13 wherein
the pressure resistant pipe section comprises a flange part on an axial end of the pressure-resistant pipe section, the flange part having a pressure-resistant infrared radiation transmissive window in the flange part with an annular seal between the transmissive window and the pressure resistant pipe section.

15. A measuring apparatus according to claim 13 wherein
the pressure resistant pipe section comprises a flange part on an axial end of the pressure-resistant pipe section, the flange part having an infrared radiation-reflecting mirror in the flange part.

* * * * *